United States Patent [19]

Evans

[11] Patent Number: 4,715,717
[45] Date of Patent: Dec. 29, 1987

[54] METHOD FOR MONITORING SURFACE TEXTURE AND QUALITY FOR MOVING TRANSPARENT FILM BODIES

[75] Inventor: John C. Evans, Midland, Mich.

[73] Assignee: The Dow Chemical Company, Midland, Mich.

[21] Appl. No.: 804,958

[22] Filed: Dec. 5, 1985

[51] Int. Cl.$^4$ ............................................. G01N 21/84
[52] U.S. Cl. .................................. 356/429; 356/430; 356/239
[58] Field of Search ............................. 356/429–431, 356/239, 237, 446–448; 250/571–572, 568

[56] References Cited

U.S. PATENT DOCUMENTS

| | | | |
|---|---|---|---|
| 3,166,627 | 1/1965 | Shaw, Jr. | 356/430 |
| 3,336,833 | 8/1967 | Villers | 356/447 |
| 4,072,426 | 2/1978 | Horn | 356/448 |
| 4,184,082 | 1/1980 | Peoples | 356/446 |
| 4,363,966 | 12/1982 | Cheo | 356/239 |
| 4,610,541 | 9/1986 | Tanimoto et al. | 356/237 |

Primary Examiner—R. A. Rosenberger
Assistant Examiner—Crystal D. Cooper
Attorney, Agent, or Firm—Timothy S. Stevens; Burk M. Halldorson

[57] ABSTRACT

The surface texture of a moving transparent film is determined by applying a beam of collimated electromagnetic radiation at an angle of incidence sufficient to produce detectable backscattered radiation; collecting the backscattered electromagnetic radiation while avoiding specularly reflected radiation; and evaluating the intensity of the collected radiation for two components, a first component corresponding to the haze percent of the film and arising from the scattering of the collimated electromagnetic radiation by microscopic and submicroscopic features of the film surfaces, and a second component produced by the scattering of the collimated electromagnetic radiation by macroscopic surface blemishes, gouges and gel-like particles on each surface of the transparent film.

11 Claims, 6 Drawing Figures

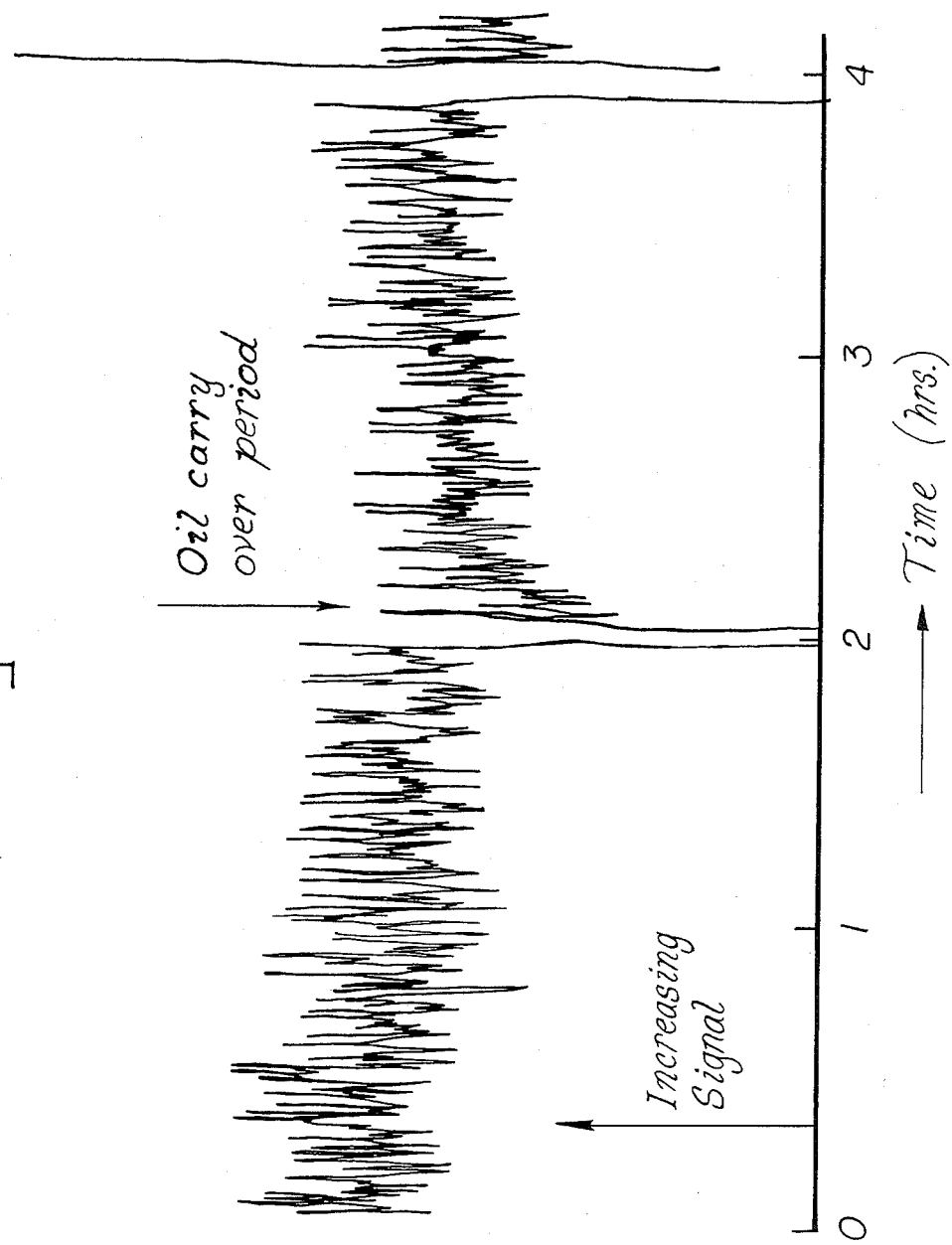

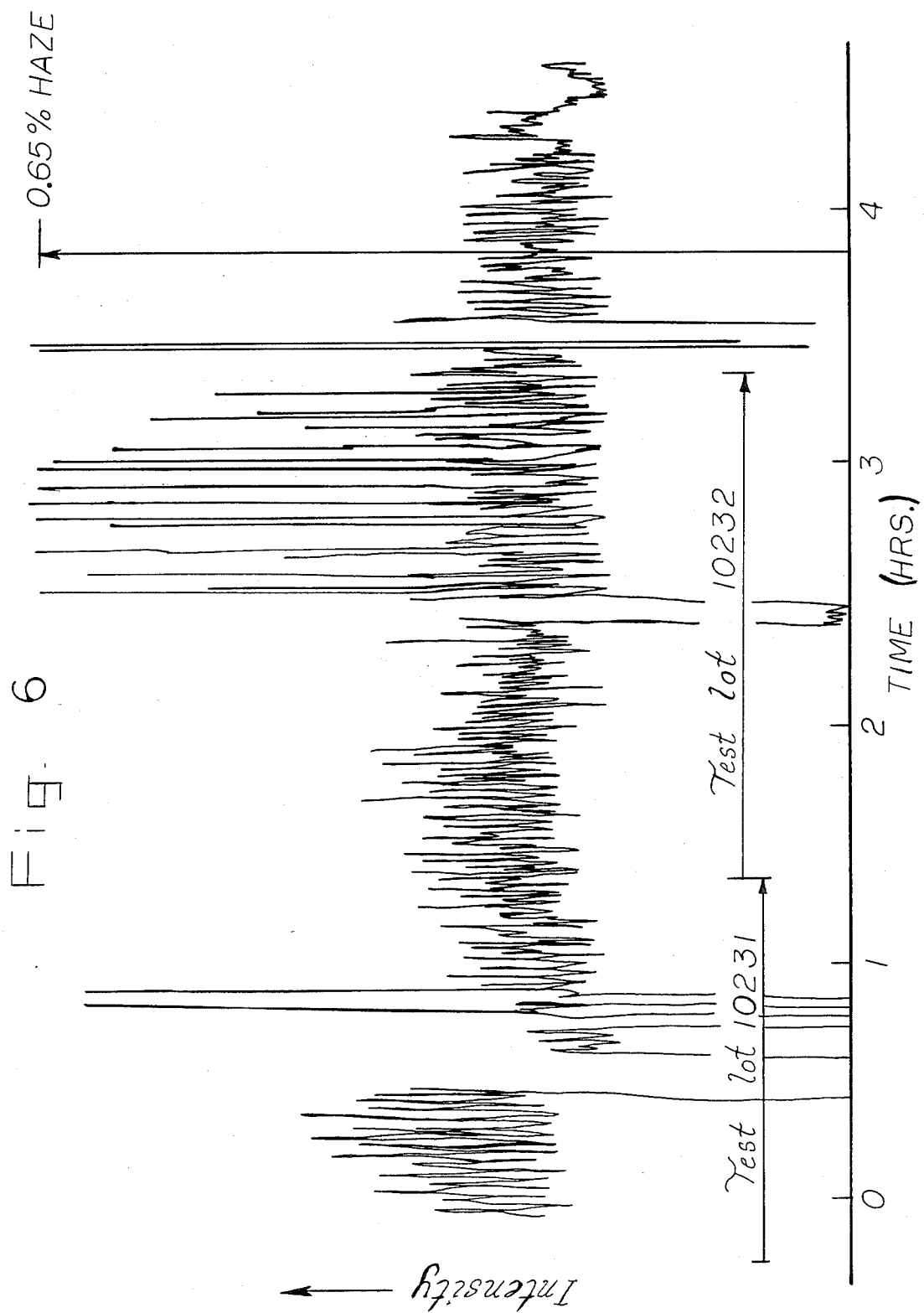

4,715,717

METHOD FOR MONITORING SURFACE TEXTURE AND QUALITY FOR MOVING TRANSPARENT FILM BODIES

BACKGROUND OF THE INVENTION

This invention relates to an electro-optical method for the inspection of a moving film body by a nondestructive, noncontact method.

Household plastic wraps, like Saran Wrap ® brand plastic film have as primary physical properties, film thickness and surface texture. Film thickness and surface texture determine the quality and the ability of the film to cling to an object. Film thickness can be controlled using on-line process monitoring devices for measuring film thickness and then manipulating the film production in accordance with the detected measurements. Film surface texture, however, is not normally measured continuously on-line and a need has existed to provide a means for continuous on-line monitoring of surface texture to obtain optimum product quality.

The detection of surface texture, particularly where the film is covered with a fluid which varies the thickness and surface conditions of the moving film body is complex. As a result, constantly changing surface conditions require intricate machinery for monitoring surface texture and film imperfections. Thus, a long felt need has existed for a simple, uncomplicated device and a simple and uncomplicated technique which can, in a single measurement, detect apparent gouges and defects on the surface of a film, such as Saran Wrap ® plastic film.

Surface texture of a moving film body can be considered in terms of surface roughness which comprises regularly occurring microscopic and submicroscopic features and irregularly occurring macroscopic features on the film body.

The optical property known as haze can be used to assess the surface texture of a plastic film body. The term "haze" refers to the intensity of light scattered at all angles greater than 2.5 degrees from the direction at which a light beam directly falls on the film. Haze is usually expressed as a percentage, that is, the "haze percent" of the light intensity transmitted directly at the film body. An optical instrument has been needed which is capable of measuring the haze percent for an essentially transparent film body having at least two surfaces which is capable of on-line measurement of the moving film body.

OBJECTS OF THE INVENTION

Accordingly, an object of the invention is to provide an electro-optical inspection system for measuring haze percent of a moving body of transparent film.

Another object of this invention is to provide an electro-optic inspection system in which inspection reliability is improved for both film product and manufacturing apparatus.

Yet another object of the invention is to provide an inspection system that transmits a light beam through the moving film body, collects the backscattered light from at least two surfaces, and then analyzes the collected backscattered light to determine the surface texture of the moving film body, particularly assessing at least two surfaces of the film body simultaneously.

SUMMARY OF THE INVENTION

The foregoing objects of this invention are achieved by the method for the on-line detection of the surface texture for a moving film body having at least two surfaces transparent to electromagnetic radiation, comprising the steps of directing a beam of collimated electromagnetic radiation at a moving film body transparent to the beam of electromagnetic radiation, at an angle of incidence sufficient to produce detectable backscattered electromagnetic radiation from the moving film body; avoiding the specularly reflected electromagnetic radiation and collecting the remaining backscattered electromagnetic radiation; directing the collected backscattered electromagnetic radiation at a detector to produce a signal proportional to the intensity of the electromagnetic radiation falling on the detector; and evaluating the detected intenstiy of electromagnetic radiation for two components, a first component corresponding to the haze percent of the film and arising from the scattering of the collimated electromagnetic radiation by microscopic and submicroscopic features of the film surfaces, and a second component produced by the scattering of the collimated electromagnetic radiation by macroscopic surface blemishes, gouges and gel-like particles on each surface of the transparent film.

The method can also be used for the on-line detection of surface fluids, the surface fluid being a member of the group consisting of plasticizers, stabilizers and mineral oil, present on the surface of a moving film body having at least two surfaces transparent to electromagnetic radiation, comprising the steps of directing a beam of collimated electromagnetic radiation at a moving film body transparent to the beam of electromagnetic radiation, at an angle of incidence sufficient to produce detectable backscattered electromagnetic radiation from the moving film body; avoiding the specularly reflected electromagnetic radiation and collecting the remaining backscattered electromagnetic radiation; directing the collected backscattered electromagnetic radiation at a detector to produce a signal proportional to the intensity of the electromagnetic radiation falling on the detector; and evaluating the detected intensity of the electromagnetic radiation for two components, a first component corresponding to the haze percent of the film and arising from the scattering of the collimated electromagnetic radiation by microscopic and submicroscopic features of the film surfaces, and a second component produced by the scattering of the collimated electromagnetic radiation by macroscopic surface blemishes, gouges and gel-like particles on each surface of the transparent film.

The invention also includes a process for the on-line detection of the surface texture for a moving film body having at least two surfaces transparent to electromagnetic radiation, comprising the steps of extruding from a die, a material suitable for forming a moving film body with at least two transparent surfaces; injecting a fluid into the extruded material to form a bubble of film; slightly deflating the bubble of film with conventional deflating means; and prior to complete deflation of the bubble, irradiating the film with a beam of collimated electromagnetic radiation at an angle of incidence sufficient to produce detectable backscattered electromagnetic radiation from the moving film body; avoiding the specularly reflected electromagnetic radiation and collecting the remaining backscattered electromagnetic radiation; directing the collected backscattered electromagnetic radiation at a detector to produce a signal proportional to the intensity of the electromagnetic radiation falling on the detector; and evaluating the detected intensity of the electromagnetic radiation for two components, a first component corresponding to the haze percent of the film and arising from the scattering of the collimated electromagnetic radiation by microscopic and submicroscopic features of the film surfaces, and a second component produced by the scattering of the collimated electromagnetic radiation by macroscopic surface blemishes, gouges and gel-like particles on each surface of the transparent film.

The method and process inventions can each include one or more of the following steps:

(A) the step wherein the specularly reflected electromagnetic radiation is avoided by collecting the back-scattered light from along the angle of incidence;

(B) the step wherein the beam of collimated electromagnetic radiation is split by beam splitter prior to being directed onto discrete portions of the moving film body;

(C) the step wherein the beam of collimated electromagnetic radiation has a wavelength in the infrared, visible or ultraviolet regions of the spectrum;

(D) the step wherein the beam of collimated electromagnetic radiation has a wavelength in the range of between about 0.3 $\mu$m and about 3 $\mu$m;

(E) the step wherein the beam of collimated electromagnetic radiation has a wavelength of about 0.63 $\mu$m;

(F) the step wherein the beam of collimated electromagnetic radiation is modulated by a modulator before being directed onto the moving film body;

(G) the step wherein said detected intensity of electromagnetic radiation is amplified by an amplifier tuned to the frequency of the modulator;

(H) the step of recording the detected intensity of the electromagnetic radiation; and (I) the step of using a laser beam as the beam of collimated electromagnetic radiation.

The method invention can be applied to test a moving film body which comprises a member of the group consisting of polymers and copolymers of polyvinyl chloride, polyethylene, oriented polystyrene, polymethyl methacrylate, and polyethylene terephthalate.

The method invention can be used to test a moving film body which is a high density plastic film.

The process invention can be applied to the measure of transparent plastic films and particularly to the measure of Dow product Saran Wrap ® plastic films.

The nature, principle and utility of the invention will become more apparent from the following detailed description when read in conjunction with the accompanying drawings, in which like parts are designated by reference numerals.

Terms

The term "transparent" refers to a film body which permits the passage of visible light so that objects may be seen on the opposite side of the film. Film bodies with haze percent values greater than 30 percent using a standard laboratory hazemeter and ASTM standards should be considered "diffusing" or "translucent" film bodies.

The term "constant intensity" refers to a nonvarying amount of energy per unit space, such as a polarized laser beam or a collimated incandescent light source.

The term "electromagnetic radiation" refers to radiation in the form of visible, ultraviolet or near infrared radiation capable of being produced in beam form, such as a laser beam.

The term "average output signal" or "averaged response" refers to a value representing the arithmetic mean of the detected intensity of electromagnetic radiation for a given sample over a discrete period of time.

BRIEF DESCRIPTION OF THE DRAWINGS

In the accompanying drawings:

FIG. 5 depicts a signal output from the apparatus of FIG. 1 for a third sample of moving film body having at least two surfaces transparent to electromagnetic radiation. This signal output can also be used to determine the presence of mineral oil on the sample of moving film body.

FIG. 6 illustrates a signal output from the apparatus of FIG. 1 for a sample of moving film body having at least two surfaces transparent to electromagnetic radiation which reveals local imperfections in the sample. This signal output illustrates a signal occurring over a period of about four hours. This signal output also illustrates imperfections in the sample of moving film body directly exposed to the beam of electromagnetic radiation.

DETAILED DESCRIPTION OF THE INVENTION

Figure 1:
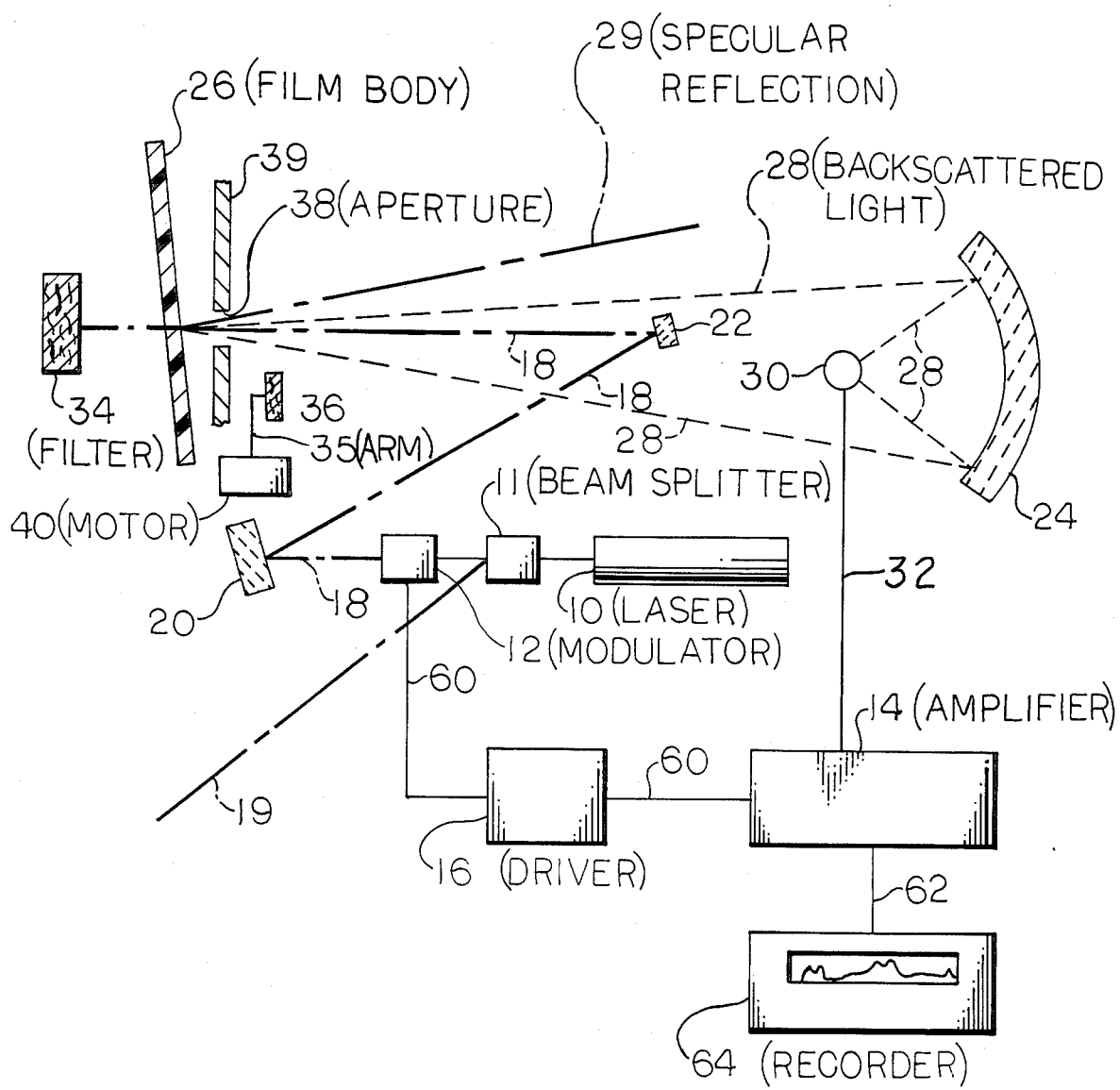
FIG. 1 is a schematic illustration of a preferred embodiment of the present invention.

Referring to FIG. 1, electromagnetic radiation in the form of visible, ultraviolet or near infrared radiation is emitted in beam form from a source 10. In the preferred embodiment, source 10 is a small class II polarized, helium-neon laser capable of 0.5 milliwatt (mw) output at 6328 Å. A polarized laser can avoid intensity variations in output which may occur when using an unpolarized laser with reflecting optics at large angles of incidence. The radiation beam is preferably modulated by a modulator 12 which in the embodiment of FIG. 1 is preferably operated at 40 Hertz. Modulator 12 can be a blackened brass leaf mounted on the oscillating axis of a small scanner motor, such as a scanner produced by General Scanning Corporation and used in conjunction with an external output of a lock-in amplifier 14 through wires 60 with a hook-up. A typical lock-in amplifier 14 usable within the scope of the present invention is sold by Princeton Applied Research, Product Number JB-5. The modulator 12 is preferably operated by a driver 16 controlled in part by lock-in amplifier 14 through wires 60. After modulation, the modulated radiation beam 18 is then directed first to a small circular plane mirror 20, and second to a small circular plane mirror 22. Mirror 22 directs the reflected modulated radiation beam 18 onto the transparent moving film body 26.

Mirror 20 in the preferred embodiment can be about 5 mm in diameter. Mirror 20 redirects the reflected modulated radiation beam onto mirror 22, which can be a small circular plane mirror about 5 mm in diameter. The small circular plane mirror 22 is preferably located in the line of sight of a large concave mirror 24.

The modulated radiation beam 18 is partially deflected by the transparent moving film body 26 creating backscattered light indicated as light beams 28 and specularly reflected light beams indicated as light beams 29. The specularly relected beams 29 are not collected by concave mirror 24. However, the backscattered light beams 28 preferably are collected by concave mirror 24. Further, concave mirror 24 directs the backscattered light beams 28 at a detector 30. Concave mirror 24, in this embodiment, preferably is a mirror with a focal length of about 160 mm and a diameter of about 100 mm.

Detector 30 is preferably a photomultiplier tube detector which is preferably protected by a narrow bandpass filter. An RCA tube with a power supply built into the base, known as Product Number IPA PF 1039 can be successfully used within the scope of this invention. Detector 30 measures the amount of backscattered light 28 directed at it, and passes this measured value to the lock-in amplifier 14 along means 32. The lock-in amplifier 14 amplifies this measured value and then presents the amplified value as a signal over wires 62, to a conventional recording means 64, such as a strip chart recorder or a computer. A computer (not shown in FIG. 1) can be used to provide a closed-loop control of the inventive process.

In this embodiment, the distance between the film and the light collecting mirror 24 is preferably as large as reasonably possible, about 60 cm, so that small variations in the position of the film do not introduce significant changes in the collection angle.

As shown in FIG. 1, the modulated radiation beam 18 can be passed through the transparent moving film body 26 and substantially absorbed by a filter 34 mounted on a frame at an angle in line with the beam. However, if filter 34 is not used, the beam 18 can pass through the film body to the building walls or ceiling, provided the walls or ceiling do not backscatter the modulated radiation beam with an intensity large enough to produce a signal at the detector 30.

FIG. 1 further contains a beam splitter 11 for splitting the laser beam from laser 10 and forming a second beam 19 which can be directed towards the moving film body. This second beam 19 can be used to test the surface texture of the moving film body at a secondary location in conjunction with the primary testing location of beam 18.

The use of a modulator 12 as a part of the apparatus invention is preferred since it is likely that in the commercial use of the apparatus invention, the measurements will be made in a well lighted factory. By using a modulator to modulate the collimated light emanating from light source 10 the diffuse reflectance readings will not be affected by the level of extraneous light present in the environment. Where a modulator 12 is utilized in the apparatus invention at a point prior to directing the beam 18 onto the transparent moving film body 26, it is desirable, subsequent to the detection of the diffuse reflection emanating from body 26, to tune amplifier 14 to the frequency of modulator 12. In this way, only the modulated portion of the backscattered light is amplified and the effect of the extraneous light falling upon transparent moving body 26 is canceled out. The circuitry necessary to provide the modulated collimated light and the amplifier tuned to the modulator frequency for amplifying the modulated detector output signal is well known in the art and no further description thereof need be made here.

In yet another embodiment, the invention can further include testing means to periodically inspect the instrument's stability. These testing means can include a reference filter 36 mounted on a rotating arm 35 driven by a clock motor 40. Preferably, the reference filter 36 is located at the aperture 38 where the modulated radiation beam 18 exits the protective enclosure of the instrument 39. The testing means operate by periodic insertion of the reference filter 36 into the beam 18 using arm 35. The constant intensity beam of electromagnetic radiation is backscattered off of filter 36 instead of transparent moving film body 26. Filter 36 preferably is an opaque material capable of backscattering about the same amount of light as from the transparent moving film body. If all components are functioning correctly the measured signal will be a constant value.

In further embodiments of the invention, a D.C. detection system (without modulation by the modulator 12) can be used in place of the A.C. detection system (with modulator 12) shown in FIG. 1. The D.C. method and apparatus are within the scope and teaching of the present invention.

The output signals from the apparatus of FIG. 1 provide information relating to the film surface texture, such as information relating to the frequency of occurrence of imperfections, such as foreign particles, polymer gel particles, surface gouges and blemishes, on the moving film body. Also, the output signals, such as those illustrated in FIGS. 2, 4, 5 and 6, provide information relative to the presence of surface liquid on the film body, the quality of different film samples relative to the output signal intensity and the presence of faults in the equipment used in manufacturing the moving film body.

Figure 2:
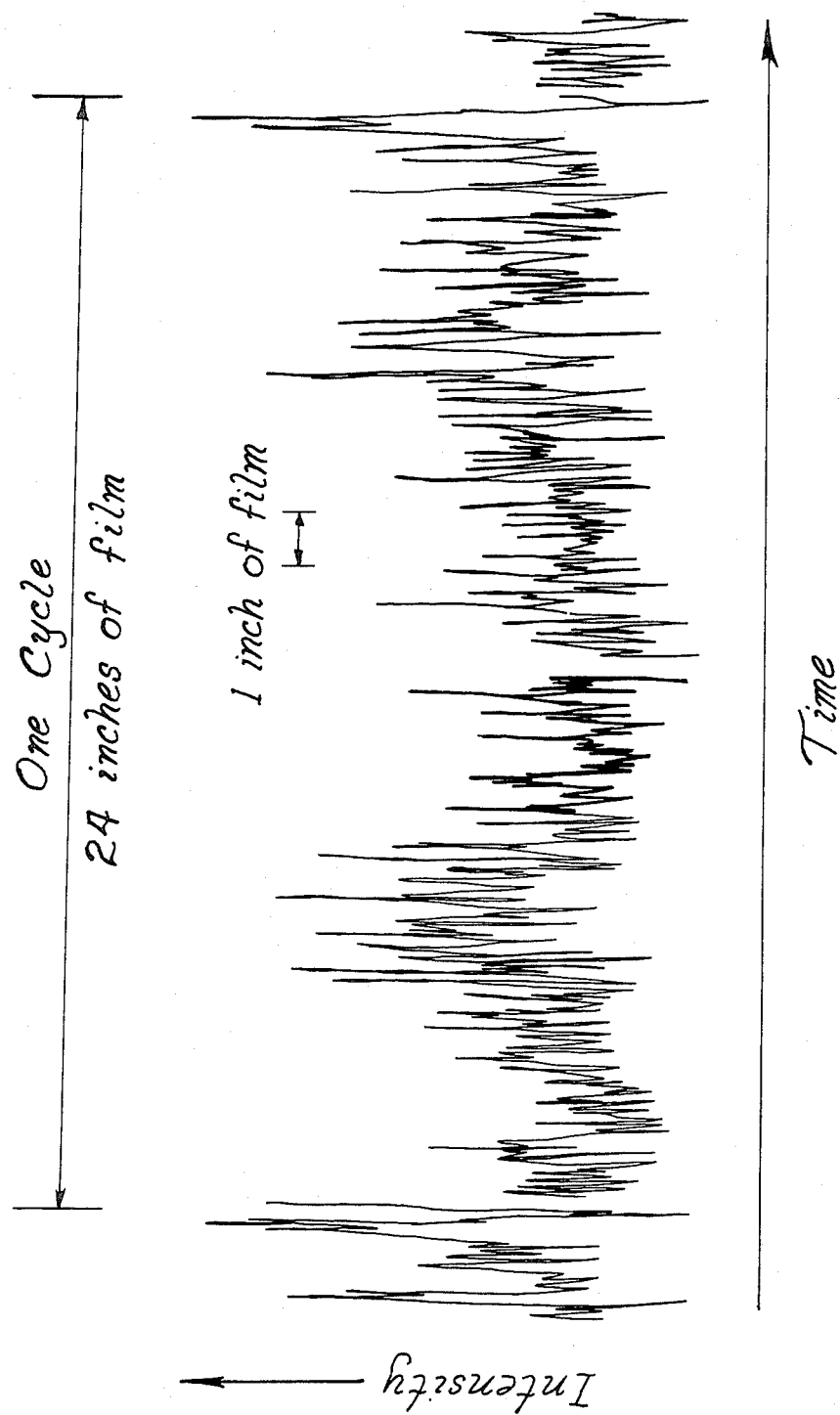
FIG. 2 illustrates a signal output from the apparatus of FIG. 1 for a sample of moving film body having at least two surfaces transparent to electromagnetic radiation which reveals local imperfections in the sample. The signal output represents a period of about 20 seconds.

FIG. 2 graphically depicts output signals resulting from practicing the method invention on a given sample during one cycle, here, a 20 second run in which a 24 inch section of transparent Dow product, Saran Wrap ® plastic film, was examined. Each spike in FIG. 2 reveals a local imperfection, of about a millimeter in size, occurring on the surface of the moving film body. The area illuminated on the film body to obtain this signal was about 1 mm². This illumination area was fixed at 1 mm² but it could have been of a greater or lesser diameter by adjusting the optical means for focussing.

Figure 3:
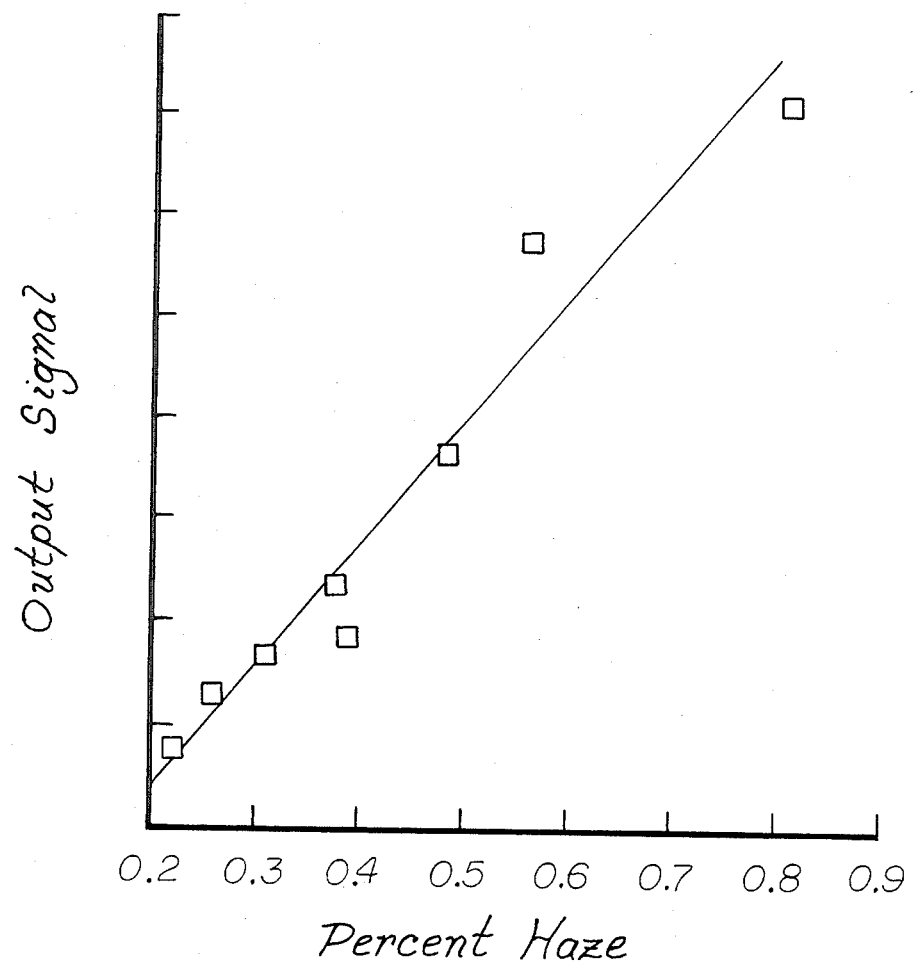
FIG. 3 depicts the calibration curve for the apparatus of FIG. 1 wherein the average response of eight different moving film bodies have been individually measured with the apparatus invention shown in FIG. 1 and the average response of the eight samples are individually plotted against a standard laboratory measurement of "haze" for each of the same eight samples.

FIG. 3 depicts a calibration curve wherein the backscattered electromagnetic radiation average output signal for each of eight samples is plotted against a percent haze value for the same eight samples. This curve is determined by using an average output signal or time averaged signal for each of the eight samples as taken over a period of several seconds (about three). The average output signal for each sample is plotted against the known "haze" property of the transparent film body as evaluated in the laboratory by means of a conventional standard commercial haze meter. This average output signal for each of the eight samples was determined using the apparatus of FIG. 1 and in particular, a He/Ne laser operated at 6328 Å, capable of producing an electromagnetic radiation beam which was modulated at a rate of 40 Hertz. The standard haze measurement was performed with a Gardner laboratory hazemeter.

The apparatus of the invention is also applicable to measuring critical aspects of the manufacturing process, as well as the surface texture and film quality described above. By establishing a relationship between the major oscillations and (a) plastic build-up or (b) failures in the extruder die face, apparatus used in the manufacturing process can also be monitored.

Figure 4:
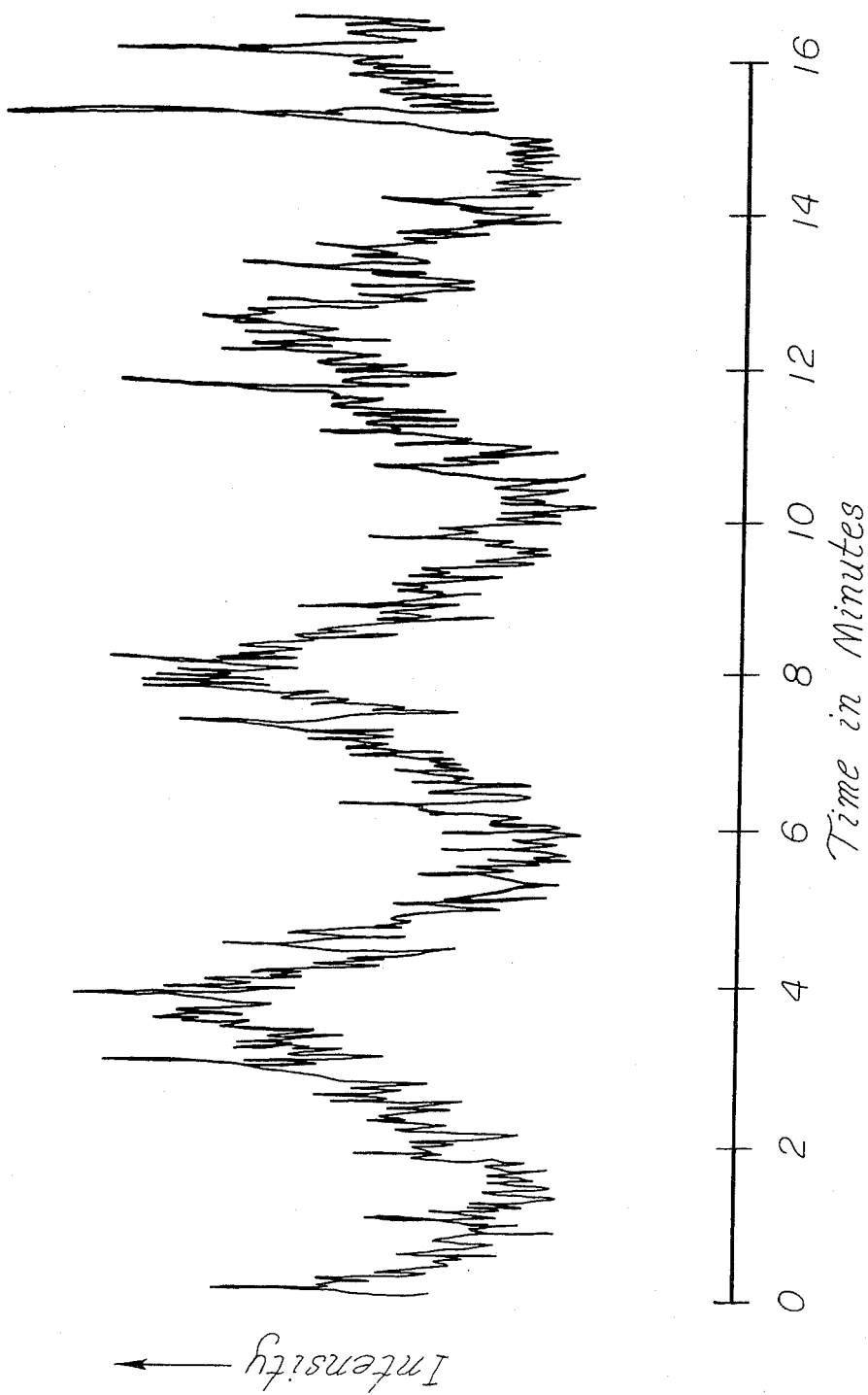
FIG. 4 illustrates a signal output from the apparatus of FIG. 1 for a second sample of moving film body having at least two surfaces transparent to electromagnetic radiation and which reveals local imperfections in the sample. The signal output can also be used for the detection of malfunctions in the manufacturing equipment used to form the sample of moving film body.

FIG. 4 illustrates a typical 20 minute output signal resulting from measurement of a given sample using the apparatus shown in FIG. 1 and illustrates a means to monitor the manufacturing apparatus use to form a moving film body. The signal shown in FIG. 4 is produced by monitoring a given transparent moving film body traveling at a rate of 200 feet per minute (ft/min) using a laser producing a beam of constant energy electromagnetic radiation at a wavelength of 6328 Å, modulated at a rate of 40 Hertz. The output signal contains major oscillations, the second component of the signal, which indicates faults in the manufacturing apparatus. The large spikes in the recorded signal indicate failures in the extruder die face to properly extrude the film. These spikes or oscillations can be used to predict major manufacturing line interruptions due to manufacturing equipment failure.

The inventive method can also be used to show that major differences exist in the quality of different batches of polymer being used in the manufacturing process. The difference in quality of sample film can be seen in marked changes in the average output signal, such as greater average output signal, or alternatively, a smaller average output signal during a discrete time period.

The invention can also be used to monitor the carry-over of oil onto the plastic film. Oil on the film smooths the surface and markedly reduces the backscattered radiation intensity. Occasional oil pick-up after line interruptions are manifested by brief periods of abnormally low signal intensity.

FIG. 5 depicts the signal output for a moving film body with oil disposed on its surface. The markedly lower average signal intensity indicates the presence of excess mineral oil on the surface of the film.

Unlike conventional haze meters, which collect and measure almost all of the forward scattered light except for a small core around the transmitted beam, applicants' invention can measure the light scattered backward into a small solid angle near to the incident beam direction.

In the following examples, a moving film body was evaluated for surface texture and surface imperfections.

EXAMPLE 1

The apparatus of FIG. 1, known as the "Surface Texture Monitor" or "STM" is assembled as described in the detailed description of the invention, and was mounted adjacent to an experimental film production line used for testing new batches of polymer. The manufacturing line was substantially the same as that described in U.S. Pat. No. 2,453,080 for the production of a Dow plastic film. The apparatus of FIG. 1 was located near the transparent film bubble where the film passes over collapsing rollers immediately prior to entering nip rollers which seal the bubble.

The instrument was calibrated in situ using film samples of measured percent-haze. Calibration was performed by mounting taut film samples held by a hoop near the instrument. An assessment of the bulk, i.e., the nonsurface contribution to the novel instrument signal, was made by comparing the signals from the inventive instrument with signals from a conventional laboratory haze meter (such as a Garner Laboratory hazemeter) after both faces of a given film sample were covered with an index matching liquid; such as Dow Corning pump oil No. 705 (having a refractive index of 1.58). The residual scattering due apparently to imperfections within the film was low in all samples, amounting only to about 10 percent on the sensitivity setting employed for all the on-line monitoring work; this was equivalent to about 0.06 percent-haze.

After calibration line speed was about 200 feet per minute (ft/min). The instrument was generally run with a 3 second time constant except for brief periods when faster variations were recorded; the recorder response, about 0.5 second, was then the limiting factor. The larger defects were evident in the signal as spikes riding on the background scattering due to the microscopic roughness.

FIG. 4 illustrates a 20 minute period examined with the fastest time constant. More interesting than the presence of the spikes is the major variation evident over the short time interval. Also apparent is the periodic nature of the variation, about 4 minutes per cycle. This coincides with the randomizer oscillation which rotates the moving film as a bubble and helps to distribute any thickness variations more uniformly. In this embodiment, the randomizer rotates the bubble through the STM beam and enables the stationary analyzer to sample the bubble completely. These and other large oscillations occurred in the absence of large oscillations in the thickness monitor's output. Typical thickness oscillations were usually within ±10 percent as measured independently by a commercial thickness monitor.

The electromagnetic radiation source was a He/Ne laser. The laser was adjusted to emit an electromagnetic beam capable of producing about 0.5 mw of 6328 Å radiation in a 1 mm beam. This beam was modulated at 40 Hertz by a conventional modulator. The recording lock-in amplifier (Princeton App. Res. J.B.-5) of this example had a time constant of about 3 seconds. The strip chart recorder was a Heath Schlumberger Model SR-255B. The signal output illustrated in FIG. 6 was taken over a four hour period. From this calibrated chart, the present haze of the film is easily determined. Among other things, the signal output reveals that large changes in the film quality occurred during a period between the line interruptions, indicated by arrows. Periodic excursions of the average haze of a sample show that certain regions of the manufactured film are excessively poor in quality and that the probable cause for these variations lies in a localized malfunction at the extruder die. The asymmetrical output of the circular die is undoubtedly the source of both thickness and surface roughness variations with the roughness being the more sensitive parameter. Asymmetry in the die gap, in the die temperature distribution, in the build-up of carbon within the die and in the build-up of slough on the external die lip, all contribute to the surface roughness variation around the extruded tube and the expanded film bubble. The novel instrument is a sensitive indicator of the condition of the extruder die.

Line interruptions due to film bubble failure are relatively frequent in this process and these account for the breaks in the record as shown in FIG. 6 where the signal falls to near zero. Frequently, but not invariably, a bubble break triggers a visual inspection of the die face by the operators and a cleaning of the die face. This may or may not involve the breaking of the extruded plastic tube and the release of some of the mineral oil/water emulsion within the tube into the film quenching bath. Bubble breaks are thus occasionally followed by marked changes in instrument signal. Changes instrument signal provide a significant technique for monitoring process conditions.

EXAMPLE 2

The apparatus of FIG. 1 was operated in the D.C. recording mode where the output of the photomultiplier tube was connected directly to a fast oscillograph (Visicorder Model 1508 with M 1000 galvanometer responsive to 600 Hertz). Neither the modulator nor the lock-in amplifier of FIG. 1 were used. With this modified detection system, samples of Dow plastic film were moved through the beam of electromagnetic radiation at the rate of 4 ft/min. The beam conditions were conditions described in Example 1. The result of this run is shown in FIG. 2. FIG. 2 illustrates a typical response for about 2 feet of a transparent moving film body. In FIG. 2, the vertical axis represents the signal intensity in arbitrary units and the horizontal axis represents time. The result is a profile of the imperfections in the transparent moving film body located along the line traversed by the beam.

EXAMPLES 3-39

Using the apparatus of FIG. 1, samples 3-9 of film were measured in the laboratory under constant conditions; the film was moving at a speed of about 4 ft/min and the instrument time constant was 3 seconds. The recorder was operated at a response time of about 0.5 seconds. The same laser of Example 1 was operated at the same process conditions as in Example 1. The beam emitted from the laser was modulated at the same rate.

For samples 3-9, the following results were produced:

TABLE I

Comparison of Average Values of Optical Parameters for Various Samples of film

| Sample | STM* Signal | Percent-Haze | Clarity | Gloss (45°) |
|---|---|---|---|---|
| 3 | 49 | 0.38 | 86 | 127 |
| 4 | 21 | 0.22 | 85 | 121 |
| 5 | 42 | 0.30 | 82 | 123 |
| 6 | 53 | 0.43 | 80 | 125 |
| 7 | 53 | 0.39 | 84 | 128 |
| 8 | 56 | 0.48 | 86 | 128 |
| 9 | 21 | 0.25 | 82 | 118 |

*STM = Surface Texture Monitor

As can be seen from Table I, clarity and gloss changes occur for the films but are much less sensitive to the surface changes than was the percent-haze measurement.

After washing the two surfaces of each sample with n-hexane, the following results were obtained:

TABLE II

| Sample | STM | Percent-Haze | (Change After Wash) |
|---|---|---|---|
| 7 | 55 | 0.41 | (little change) |
| 8 | 93 | 0.56 | (major change) |
| 9 | 212 | 0.80 | (major change) |

As Table II demonstrates, there was a dramatic increase in surface scattering when the oil layer filling the imperfections in the surface structure was removed. Film sample 8, initially had a 0.27 percent-haze reading. After washing, the haze value changed to 0.56 percent haze (after washing one face). After washing the second face, the haze value increased to 0.68 percent. Film sample 7 showed an initial haze value of 0.39 percent-haze, which became 0.41 after the first face was washed and 0.80 after the second face received its wash.

It will be apparent to those skilled in the art that the basic apparatus of the present invention may be modified by mechanical changes, such as using larger diameter mirrors or a more narrow beam of light. It should be understood that modifications of this nature are intended to be within the scope of this invention, if not literally, then by the Doctrine of Equivalents by which the inventor states his intent to rely on construction of the scope of his claimed invention below.

Statement of Intent

The inventor hereby states his intent to rely on the Doctrine of Equivalents to determine and assess the fair scope of his invention as set out and defined in the following claims.

What is claimed is:

1. A method for online detection of surface texture of a moving transparent film body, comprising the steps of:
   extruding from a die, a material suitable for forming the moving transparent film body;
   injecting a fluid into the extruded material to form a bubble of the moving transparent film body;
   slightly deflating the bubble with conventional deflating means;
   prior to complete deflation of the bubble, irradiating the moving transparent film body with a beam of collimated electromagnetic radiation at an angle of incidence sufficient to produce detectable backscattered electromagnetic radiation and specularly reflected electromagnetic radiation from said moving transparent film body;
   avoiding the specularly reflected electromagnetic radiation and collecting the backscattered electromagnetic radiation;
   directing the collected backscattered; electromagnetic radiation to a detector to produce a signal proportional to the intensity of the collected backscattered electromagnetic radiation directed to the detector; and
   evaluating the signal so that the surface texture can be detected.

2. The process of claim 1, wherein said specularly reflected electromagnetic radiation is avoided by collecting the backscattered electromagnetic radiation from along the angle of incidence.

3. The process of claim 1, wherein said beam of collimated electromagnetic radiation is split by a beam splitter prior to being directed at the moving transparent film body.

4. The process of claim 1, wherein said beam of collimated electromagnetic radiation has a wavelength in the infrared, visible or ultraviolet regions of the spectrum.

5. The process of claim 4, wherein said beam of collimated electromagnetic radiation has a wavelength in the range of between about 0.3 $\mu$m and about 3 $\mu$m.

6. The process of claim 5, wherein said beam of collimated electromagnetic radiation has a wavelength of about 0.63 $\mu$m.

7. The process of claim 1, wherein said beam of collimated electromagnetic radiation is modulated by a modulator before being directed onto the moving transparent film body.

8. The process of claim 7, wherein said signal is amplified by an amplifier tuned to the frequency of said modulator.

9. The process of claim 1, further comprising the step of recording the signal.

10. The process of claim 1, wherein said moving transparent film body comprises a member of the group consisting of polymers and copolymers of polyvinyl chloride, polyvinylidine polyethylene, oriented polystyrene, polymethyl methacrylate, and polyethylene terephthalate.

11. The process of claim 1, wherein said moving film body is a high density plastic film.

* * * * *

UNITED STATES PATENT AND TRADEMARK OFFICE
CERTIFICATE OF CORRECTION

PATENT NO. : 4,715,717

DATED : December 29, 1987

INVENTOR(S) : John C. Evans

It is certified that error appears in the above-identified patent and that said Letters Patent is hereby corrected as shown below:

Col. 9, line 13, insert -- in -- after the second occurrence of "changes";

line 27, insert -- identical to the -- after "were";

line 37, "3-39" should read -- 3-9 --.

Col. 10, line 54, delete the semicolon after "backscattered".

Col. 12, line 9, insert -- chloride, -- after "polyvinylidine".

Signed and Sealed this

Eighth Day of November, 1988

Attest:

DONALD J. QUIGG

*Attesting Officer*  Commissioner of Patents and Trademarks